United States Patent [19]

Gibson

[11] Patent Number: 4,647,701

[45] Date of Patent: Mar. 3, 1987

[54] PROCESSES FOR PRODUCING DIETHYLENETRIAMINE FROM MONOETHANOLAMINE

[75] Inventor: Charles A. Gibson, South Charleston, W. Va.

[73] Assignee: Union Carbide Corporation, Danbury, Conn.

[21] Appl. No.: 613,473

[22] Filed: May 23, 1984

[51] Int. Cl.[4] .............................................. C07C 85/06
[52] U.S. Cl. .................................... 564/479; 564/480; 564/512
[58] Field of Search ........................ 564/512, 479, 480

[56] References Cited

U.S. PATENT DOCUMENTS

| | | | |
|---|---|---|---|
| 2,861,995 | 11/1958 | MacKenzie | 544/358 |
| 3,151,115 | 9/1964 | Moss et al. | 564/503 |
| 4,111,840 | 9/1978 | Best | 564/480 |

FOREIGN PATENT DOCUMENTS 149509 7/1981 German Democratic Rep. .

OTHER PUBLICATIONS

U.S. Ser. No. 454,485, filed Dec. 29, 1982.

*Primary Examiner*—Paul F. Shaver
*Attorney, Agent, or Firm*—Morris N. Reinisch

[57] ABSTRACT

Ethanolamine is subjected to reductive amination in a continuous process to produce diethylenetriamine with less than 10 weight percent piperazine contained in the reaction products. The reductive amination conditions include the use of a catalyst, an ethanolamine feed rate of at least about 400 kilograms of ethanolamine per hour per cubic meter of catalyst, and a temperature sufficient to react between about 35 and 60 percent of the ethanolamine fed.

14 Claims, No Drawings

PROCESSES FOR PRODUCING DIETHYLENETRIAMINE FROM MONOETHANOLAMINE

This invention relates to processes for enhancing the production of diethylenetriamine from monoethanolamine and ammonia. By this invention, processes are provided that enable desirably high conversion of monoethanolamine to diethylenetriamine without the production of untoward amounts of cyclic products such as piperazine and aminoethylpiperazine. Ethylenediamine is also produced in accordance with the processes of this invention.

BACKGROUND TO THE AMINATION OF MONOETHANOLAMINE

The amination of monoethanolamine with ammonia in the presence of a hydrogenation catalyst to produce ethylenediamine is well known and is commercially practiced. These processes generally produce other products such as aminoethylethanolamine, diethylenetriamine, piperazine, and aminoethylpiperazine. A general background on the production of ethylenediamine for monoethanolamine is provided by M. Arne, "Alkyl Amines", Process Economics Progress Report No. 138, SRI International, dated March, 1981, see particularly the section entitled "Ethyleneamines from Monoethanolamines".

A troublesome problem with the amination of monoethanolamine to make ethylenediamine has been the coproduction of significant amounts of by-products, particularly cyclic amines, especially piperazine and aminoethylpiperazine, that are of less commercial value than ethylenediamine.

Not only are piperazine and other cyclics formed, but such formation consumes the desired ethylenediamine. To avoid the formation of cyclic amines, the usual approach has been to reduce the overall ethylenediamine yields. For example, U.S. Pat. No. 3,068,290, states at column 4, lines 27 to 36;

"The condensation products [e.g., piperazine] are essentially formed at the expense of the ethylenediamine itself so that, as the transformation of monoethanolamine is going on, the transformation of the condensation products reverses and the ethylenediamine output decreases. The simplest method for limiting the ethylenediamine concentration, thereby the formation of its condensation products, consists in limiting the transformation of the monoethanolamine, the unchanged product being used then as a diluent."

U.S. Pat. No. 4,111,840, states at column 10, line 40 to 44:

"Where selectivity is of primary concern in the amination process, it is preferred not to run the process to a high conversion. It has been found that selectivity to the preferred aminoalkanes decreases as conversion increases."

The potential to aminate ethanolamine to produce diethylenetriamine in addition to ethylenediamine and piperazine is well known. For instance, U.S. Pat. No. 2,861,995 asserts at column 2, lines 13 to 16, that "Generally, between about 5 and 20 percent of the converted ethanolamine may be obtained as diethylenetriamine, depending on the particular conditions that may be involved."

The patent further states at column 2, lines 7 to 13, that

"... the amount of piperazine yield may be reduced almost to the vanishing point, if it is undesirable for any reason to obtain such a product at the expense of higher ethylenediamine yields, by utilizing lower temperatures, greater quantities of ammonia and lesser relative amounts of the catalyst or shorter catalyst contact times."

Again, the approch is one of reducing ethylenediamine yields to avoid piperazine production. The patent provides three examples which are summarized in the following table. In each example, the amount of Raney nickel catalyst used was 3.1 pounds. The ethanolamine conversion for the first run set forth in the table was reported to be 75 percent. The conversion for the other runs was not provided. However, the patent relates at column 1, lines 50 to 55 that conversions of 70 to 80 percent are readily achieved.

| Ethanolamine Feed Rate lbs./hr. | Ethanolamine to Ammonia Mole Ratio | Temperature °C. | Pressure, psig | Products as % of Converted Ethanolamine | | |
|---|---|---|---|---|---|---|
| | | | | Ethylenediamine | Piperazine | Diethylenetriamine |
| 2.2 | 1:3.5 | 195 | 1950 | 24.1 | 29.8 | 14.52 |
| 1.6 | 1:3.3 | 160–170 | 1950 | 50.5 | 12.5 | 9.3 |
| 2.64 | 1:5.6 | 165 | 1500 | 60.8 | about nil | 16.34 |

The patent also states at column 3, lines 20 to 22, that

"Conditions favoring greater conversions to piperazine also tend to minimize the production of higher amine products."

Examples 1 to 5 of U.S. Pat. No. 3,151,115 employ a nickel-copper-chromium catalyst under differing process conditions for the conversion of monoethanolamine and ammonia to various amination products. The examples illustrated different temperatures for ammonia and monoethanolamine feed rates, and the effect of the addition of water. With process conditions favoring the formation of linear amines, considerable amounts of aminoethylethanolamine were reported to be produced. The examples can be summarized as follows:

| | Example | | | | |
|---|---|---|---|---|---|
| | 1 | 2 | 3 | 4[1] | 5[1] |
| Reactor temp., °C. | 199 | 198 | 198 | 223 | 227 |
| Hydrogen rate; SCFH | 800 | 800 | 800 | 800 | 800 |
| Reaction press., psig. | 2,800 | 2,800 | 2,800 | 2,800 | 2,800 |
| Feed rates, gal./hr.: | | | | | |

-continued

|  | Example | | | | |
|---|---|---|---|---|---|
|  | 1 | 2 | 3 | 4[1] | 5[1] |
| NH₃ (anhydrous) | 94 | 70 | 47 | 80 | 80 |
| Monoethanolamine (MEA) | 35.5 | 25.5 | 16 | 158 | 158 |
| NH₃/MEA mol. ratio | 5.6 | 5.8 | 6.2 | 1.1 | 1.1 |
| Space velocity, g/hr, ml. cat. | 6.2 | 4.5 | 3.0 | 3.1 | 3.1 |
| Conversion of MEA, % | 29.3 | 39.8 | 53.8 | 71.4 | 75.4 |
| Yields (molar), %: | | | | | |
| Ethylenediamine | 41.3 | 38.5 | 36.2 | 12.0 | 15.0 |
| Piperazine | 13.7 | 18.7 | 23.2 | 47.6 | 58.0 |
| Diethylenetriamine | 7.1 | 7.6 | 9.3 | 9.0 | 3.3 |
| N—Aminoethylpiperazine | 2.1 | 3.0 | 3.0 | 15.0 | 17.5 |
| Aminoethylethanolamine | 22.3 | 18.4 | 13.2 | — | — |
| Hydroxyethylpiperazine | 0.5 | 2.2 | 3.2 | 6.0 | 3.5 |
| Residue | 12.0 | 11.6 | 11.9 | 10.4 | 2.7 |

[1] Also used 140 gal. water/hr. in feed.

Russian Pat. No. 545,633 discloses a process for the amination of monoethanolamine using a nickel on chromium oxide catalyst to produce various polyamines. Examples 1 to 4 of that patent can be summarized as follows. In Examples 1, 2 and 4, the catalyst contained 50% nickel and 32% chromium oxide and in Example 3, 44% nickel and 51% chromium oxide.

|  | Example | | | |
|---|---|---|---|---|
|  | 1 | 2 | 3 | 4 |
| Amount of Catalyst, cm³ | 100 | 50 | 50 | 50 |
| H₂ pressure, atm | 160 | 120 | 160 | 160 |
| Temperature, °C. | 200 | 170 | 200 | 200 |
| Monoethanolamine feedrate, cm³/hr | 70 | 35 | 23 | 23 |
| Monoethanolamine conversion, % | 60.7 | 40.0 | 80 | 32 |
| Products, % based on reacted monoethanolamine | | | | |
| Ethylenediamine | 52.2 | 60.6 | 46.0 | 88.0 |
| Piperazine | 25.8 | 16.0 | 37.9 | 12.0 |
| Substituted piperazine | 13.9 | 7.4 | 7.0 | — |
| Aminoethylethanolamine | 5.5 | 11.2 | — | — |
| Diethylenetriamine | 2.6 | 2.7 | 5.2 | — |

As can be seen from these examples, conditions that favor diethylenetriamine production favor the formation of piperazine and disfavor the production of ethylenediamine.

East German Pat. No. 149,509 relates to a method for making polyethylene polyamines from ethylene oxide and ammonia without isolating or separating intermediate products. The product from the ethylene oxide and ammonium reaction is directly fed to an amination reaction zone containing hydrogenation catalyst at 150° to 210° C. The total process is stated to be conducted in a single up-flow reactor vessel. The pressure is maintained sufficiently high that a liquid phase is maintained in all reaction zones. The authors state that the amount of hydrogenation catalyst is selected based on the desired polyamine with liquid hourly space velocities of about 0.5 to 3 based on liquid product. Since the reaction is conducted in a single vessel, ethylene oxide can be expected to be present during the amination and relatively large amounts of oxygen-containing products such as diethanolamine, thiethanolamine, and aminoethylethanolamine, and it can also be expected that relatively small amounts of ethylenediamine will be present. This expectation is bourne out by the examples which are summarized below.

| Component (mole %) | Example | | |
|---|---|---|---|
|  | 1 | 2 | 3 |
| Monoethanolamine | 34.6 | 15.8 | 24.6 |
| Diethanolamine | 10.8 | 12.1 | 10.3 |
| Triethanolamine | 1.5 | 3.2 | 2.8 |
| Ethylenediamine | 11.9 | 8.3 | 9.4 |
| Diethylenetriamine | 15.2 | 21.6 | 20.8 |
| Aminoethylethanolamine | 12.1 | 9.6 | 14.0 |
| Piperazine | 7.8 | 10.2 | 6.8 |

Diethylenetriamine is a well-recognized starting material for the formation of piperazine. See, for example, U.S. Pat. Nos. 2,267,686 and 2,809,195. In U.S. Pat. No. 2,901,482, a continuous process for making piperazine from diethylenetriamine is disclosed. The patentees note that the gas hourly space velocity for producing piperazine using a fixed bed of, e.g., Raney nickel catalyst is about 1 to 3 reciprocal hours.

N-aminoethylethanolamine is also a product that can be produced by the amination of monoethanolamine in the presence of ammonia. It is recognized that this product can readily form piperazine. For example, in Japanese Patent Application Kokai No. 49/11712, a copper and chromium-containing catalyst is disclosed for making piperazine from aminoethylethanolamine with high yields and selectivities.

When linear polyethylene polyamines are the desired product with the minimization of the production of cyclic amines such as piperazine, other types of processes such as the amination of ethylene dichloride have been employed. Another type of process is disclosed in U.S. Pat. No. 3,714,259. The patent describes a process for making linear polyethylene polyamines by reacting an ethyleneamine with an ethanolamine under certain process conditions including the essential absence of ammonia. The process is described as catalytic using a hydrogenation catalyst and is conducted under conditions such that the reactants are maintained in the liquid phase. See also U.S. patent application Ser. No. 454,485, filed Dec. 29, 1982, of Frank G. Cowherd III, herein incorporated by reference, which discloses the reaction of ethylenediamine with or without monoethanolamine under certain process conditions including conversions of less than about 35 percent to produce diethylenetriamine and minimize the formation of piperazine.

Although numerous processes have been disclosed for making ethylenediamine and/or piperazine by the amination of monoethanolamine, the production of diethylenetriamine by this route has generally been incidental. Little flexibility has existed in providing an amination product mix that maximizes diethylenetriamine production without undue sacrifice in ethylenediamine production while minimizing the production of cyclic amines such as piperazine and oxygen-containing amines such as aminoethylethanolamine. Indeed, the emphasis of many prior workers in the field has been to minimize piperazine formation by reducing the conversion of monoethanolamine to amine products. Such process directions have clear disadvantageous economic and processing features.

SUMMARY OF THE INVENTION

By this invention, processes are provided for the reductive amination of monoethanolamine with high conversions of monoethanolamine to linear ethyleneamines having enhanced production of diethylenetriamine. Desirably, the enhanced diethylenetriamine production can be achieved without the undue loss of ethylenediamine production. In advantageous aspects of this invention the amounts of piperazine produced can be maintained relatively low despite the enhanced production of diethylenetriamine. Furthermore, the processes of this invention are often readily retrofitable into existing process equipment for the amination of monoethanolamine using ammonia, and many reductive amination catalysts are suitable for use in processes of this invention. Hence, the processes of this invention provide the flexibility sought to produce an amination product mixture of increased market value in a commerically feasible manner.

In accordance with this invention, the process is conducted at a continuous feed rate of at least about 400 kilograms of ethanolamine per hour per cubic meter of reaction zone volume containing catalyst (herein referred to as the "ethanolamine feed rate") and at a temperature sufficient to react between about 35 and 60, preferably between about 38 and 58, say, about 45 and 55, percent of the ethanolamine fed (herein referred to as the "ethanolamine conversion rate"). The feed rate is preferably maintained such that, based on the total amine-containing reaction products, less than about 10 weight percent piperazine is produced. Most advantageously, the feed rate of ethanolamine is below that which results in undue amounts of aminoethylethanolamine being provided in the reaction product (i.e., total amine-containing compounds derived from the ethanolamine converted). In most instances, the product of the weight percent aminoethylethanolamine in the reaction product and the ethanolamine conversion rate in percent is less than about 600.

DISCUSSION

Reductive amination processes involve providing a feed containing monoethanolamine, ammonia and hydrogen to a reaction zone containing reductive amination catalyst at an elevated temperature sufficient to replace the hydroxyl group with an amine functional group. The processes can be affected by many variables, e.g., pressure, ammonia to ethanolamine ratio, hydrogen to ammonia ratio, temperature and the presence of other materials in the feed to the reaction zone.

An important aspect of the processes of this invention is maintaining an ethanolamine conversion rate within the prescribed ranges. Many factors come to bear in determining an ethanolamine conversion rate. Importantly, the processes of this invention employ an ethanolamine feed rate of at least about 400 kilograms per cubic meter. As a general rule, as the ethanolamine feed rate is increased, one or more other process variables must be changed such as increasing catalytic activity or temperature in order to maintain a given ethanolamine conversion rate. Most commonly, a given ethanolamine conversion rate is maintained by an increase in temperature with an increase in the ethanolamine feed rate.

In accordance with this invention, the amount of diethylenetriamine produced generally tends to increase with increased ethanolamine feed rates, but the rate of increase slows. At very high ethanolamine feed rates, the amount of diethylenetriamine produced may actually decrease depending upon the ethanolamine conversion rate. Typically the ethanolamine feed rate is maintained below the point of diminishing returns so that economic penalties such as energy consumption in passing the feed through the reactor will not off-set any benefit.

The preferred maximum ethanolamine feed rate will also be affected by the performance of the reductive amination catalyst. Catalysts exhibiting greater activities can usually provide greater rates of increase in the production of diethylenetriamine over a wider range of ethanolamine feed rates than do less active catalysts.

A particularly convenient method for evaluating the activity of a catalyst when used in processes of this invention is by the weight percent of aminoethylethanolamine that is present in the reaction product at a given ethanolamine conversion rate. The presence of relatively large amounts of aminoethylethanolamine is believed to be indicative of whether a catalyst is sufficiently active to handle an ethanolamine feed rate. Desirably, the ethanolamine feed rate is below that at which the amount of the aminoethylethanolamine, in percent based on the reaction product, times the ethanolamine conversion rate (hereinafter referred to as the "AEEA index") is less than about 600. Most often, the AEEA index is less than about 550 and ranges from between about 100 and 500. In many instances, the ethanolamine feed rate is within the range of about 400 and 1500, say, about 450 and 1000, kilograms per hour per cubic meter.

At the ethanolamine feed rates employed in the processes of this invention, it is apparent that relatively high temperatures for this type of amination of ethanolamine must be used to maintain the appropriate conversion rate. The temperatures are preferably less than 250° C., and most often are below 225° C. While relatively low temperatures, e.g., 120° C. or even less, can be used for amination reactions, such low temperatures are not preferred. It is anticipated that temperatures in excess of 150° C. will be required to achieve the appropriate ethanolamine conversion rate. Frequently, the temperatures range from about 150° C. to 225° C., e.g., about 160° C. to 210° C., and, with more active catalysts, temperature in some instances from about 170° C. to 200° C. may be suitable. In accordance with an aspect of the invention, the temperature is maintained in the range of about 170° C. to 190° C. with the ethanolamine feed rate being adjusted to obtain the desired ethanolamine conversion rate.

The feedstream to the amination reaction zone comprises monoethanolamine, ammonia and hydrogen. Generally the feedstream comprises monoethanolamine derived from the reaction of ethylene oxide and ammonia. This reacton product may be purified or may be used as the effluent. The normal by-products of the reaction between ethylene oxide and ammonia include diethanolamine and triethanolamine which tend to form cyclic amines during amination. For purposes herein, the ethanolamine feed rate is the feed rate of the total ethanolamines. Preferably, monoethanolamine comprises at least about 70 or 85 mole percent of the total ethanolamine passed to the reaction zone. A particularly attractive method for enhancing the concentration of monoethanolamine in the feed is by separating and recycling monoethanolamine from the amination reaction to the feed such as is described in U.S. Pat. No. 4,400,539, herein incorporated by reference.

The amination reaction feedstream can contain other amine and alcohol components. Because of the selectivity to diethylenetriamine and low production of cyclic amines provided by this invention, it can be attractive to add to the feed amines such as ethylenediamine for conversion to diethylenetriamine or other higher ethyleneamines. In such circumstances the total ethyleneamine component in the feed is usually up to about 5 moles per mole of total ethanolamine. Most preferably, the mole ratio of total ethyleneamines to total ethanolamine is about 0.05:1 to 2:1, say, about 0.1:1 to 1:1. Other alcohol compounds which may be in the feed include ethylene glycol and diethylene glycol; however, these components tend to form cyclic amines such as piperazine and morpholine and are consequently avoided unless such products are additionally sought.

The feed to the reaction zone also comprises ammonia. Stoichiometrically, one molecular unit of ammonia or amine (primary or secondary) is required per molecular unit of hydroxyl group. However, the formation of linear ethyleneamines is favored by the presence of excesses of ammonia, but a practical limit on the amount of ammonia employed exists due to energy consumption. Therefore, the mole ratio of ammonia to total ethanolamine is frequently at least about 2:1 or 3:1, say, about 3:1 to 30:1, e.g., about 4:1 to 25:1, and in some instances, about 10:1 to 20:1.

Hydrogen is also provided to the amination reaction zone. Typically, hydrogen is provided in an amount of at least about 2 mole percent based on the total moles of ammonia, and often this percentage is between about 2 to 20, say, about 4 to 12, percent.

The amination reaction feedstream may also contain a limited amount of water. The water that is present will typically be that which is provided as a result of ethylene oxide-ammonia reaction. The water content in the amination feed stream may range between 0 weight percent to about 10 or more weight percent, based on the weight of the amination feedstream and preferably the water content is kept between about 0 to 5 weight percent, based on the total weight of the amination feedstream. Inert gases can also be supplied to the reaction such as nitrogen, helium, methane, and the like. Such inert gases can be utilized to help in the control of the reaction temperature and assist in maintaining the desired pressure.

The reaction is conducted under elevated pressure. Often the pressure is at least about 20 atmospheres absolute, say, about 35 to 400, e.g., about 40 to 200, atmospheres absolute.

The processes of this invention can be conducted in the liquid or gas phase. For purposes herein, the term gas phase encompasses both the vapor phase and supercritical phase. While it is possible to conduct the process when the reaction mixture contains components both in the liquid and gas phases, it is generally preferable to use an amination reaction feedstream that is in a homogeneous phase. The processes of this invention are particularly useful in operations in which the amination reaction feedstream is in the gas phase. In any event, the pressure should be selected such that the amination reaction feedstream is maintained in the desired phase. In instances where the amination reaction feedstream is maintained in the gas phase, the gas hourly space velocity based on the total feed and volume of reactor containing catalyst is at least about 10 recrprocal hours, and is often in the range of about 10 to 100, say, about 12 to 60, say, about 15 to 40, reciprocal hours.

The amination zone contains reductive amination catalyst. Reductive amination catalysts are well-known in the art and comprise the metal or oxide of one or more of nickel, copper, cobalt, iron and the like as the active species. Other compounds which may find use in such catalysts include the metal, oxide or salt of one or more of chromium, lanthanum, lithium, potassium, cesium, cerium, ruthenium, rhodium, palladium, platinum, rhenium, iridium, silver, zinc, titanium, manganese and boron. Often the catalysts are of the Raney nickel-type or Raney cobalt-type, or are supported catalysts. Many of the catalysts are preferably activated at elevated temperatures in a hydrogen atmosphere. Particularly desirable catalysts comprise nickel as the catalytically-active species.

U.S. Pat. Nos. 4,111,840 and 4,123,462, both herein incorporated by reference, disclose supported catalysts containing nickel and rhenium and nickel, rhenium and boron for amination, e.g., of ethanolamines. U.S. Pat. No. 3,766,184, herein incorporated by reference, discloses amination catalysts comprising nickel, cobalt and iron. Catalysts containing nickel, cobalt and copper are disclosed in U.S. Pat. No. 4,014,933, herein incorporated by reference.

Generally, the catalysts are supported catalysts with the active species provided on the surface of the support through, e.g., coating or impregnation. The metal components on the support often comprise about 1 to 50, say, about 3 to 30, weight percent of the catalyst. Support materials are preferably inert and include aluminas, especially alpha-alumina; silica-aluminas; silica; diatomaceous earth; kieselguhr; silica-titania; and the like. Useful supports may be porous and have surface areas of from about 0.1 to 500, say, about 0.3 to 100, square meters per gram.

The catalyst may be of say convenient size or shape. Catalysts can be made in the form of powders, spherical or conical pellets, extruded strips and the like. Often, for commercial-scale operations, the pellets range in diameter from about 0.1 to 1 centimeter.

The processes of this invention are conducted in a continuous manner with the reactor feed being passed through a bed of particulate catalyst. The reactor may be an up-flow or down-flow reactor and may have a fluidized bed or, most commonly, a fixed bed. The catalyst bed may contain inert particles which may be interspersed throughout the bed and/or form discrete layers, e.g., at an end or intermediary to the bed. The volume of the reaction zone containing such inert particles is not reaction zone volume for purposes of determining the ethanolamine feed rate. Preferably, the space velocity should not be so high that for the reactor geometry, a significant amount of backmixing occurs. Advantageously, the flow through the catalyst bed is substantially plug-type flow.

ILLUSTRATIVE EMBODIMENTS

The processes of this invention were demonstrated using a high pressure reactor vessel. The reactor vessel is tubular having an outside diameter of 1 inch (2.54 centimeters), an inside diameter of 0.667 inch (1.72 centimeters), and a length of 78 inches (198 centimeters) and is constructed of stainless steel (316). The effective volume of the vessel is 400 milliliters. The vessel has two separate 500 watt windings for heating and is insulated for 300° C. service.

The system is provided with a stainless steel, tubular (2.54 centimeters outside diameter) vaporizer for the reaction feed mixture and a similar tubular vessel as an entrainment separator. Both are equipped with a 500 watt winding for heating and are insulated for 300° C. service. The system is also equipped with preheaters for the liquid and gas reactants, a pressure control system, and product collection systems. The system is adapted to be pressurized with nitrogen. At start-up, the system is typically pressurized with nitrogen which provides a diluent for the hydrogen feed until the ammonia feed is initiated.

The feed mixture for these runs is 83.60 weight percent monoethanolamine, 3.96 weight percent diethanolamine, 0.44 weight percent triethanolamine and 12.00 weight percent water. The catalyst was a silica support identified as T-869 available from United Catalysts Inc., Louisville, Ky., having thereon 6.4 weight percent nickel, 1.6 weight percent rhenium and 1.2 weight percent boron. Example 6 of U.S. Pat. No. 4,123,462 discloses a typical technique for catalyst preparation.

In Runs 5, 6 and C-6, the volume of the reactor vessel was approximately one-half filled with catalyst. In Runs 2, 3, 4 and C-3, C-4 and C-5, the volume of the reactor was approximately one-half filled with catalyst with the top one-half being filled with alundum spheres (0.47 millimeter diameter). In Run 1, the reactor volume was filled with a substantially uniformly admixed equivolume mixture of catalyst and carrier. The carrier was identical to that used to make the catalyst except it had been pretreated to contain about 5 weight percent $B_2O_3$ based on the weight of the carrier.

to 200 atmospheres absolute and a temperature between about 150° and 225° C.

5. The process of claim 4 wherein the amination feedstream is provided at a rate sufficient to provide about 450 to 1000 kilograms of ethanolamine per hour per cubic meter of reaction zone containing catalyst.

6. The process of claim 4 wherein in the amination feedstream the mole ratio of ammonia to ethanolamine is about 4:1 to 25:1 and the hydrogen is provided in an amount of about 4 to 12 mole percent based on ammonia.

7. The process of claim 6 wherein the reductive amination catalyst comprises nickel.

8. The process of claim 4 wherein the amination feedstream comprises ethylenediamine.

9. The process of claim 4 wherein the process is conducted in the gas phase and the gas hourly space velocity of the amination feedstream is in the range of about 12 to 60 reciprocal hours.

10. A process for producing diethylenetriamine from ethanolamine containing at least about 85 mole percent monoethanolamine comprising continuously passing in the gas phase an amination feedstream comprising the ethanolamine, ammonia and hydrogen over a reductive

| Run | Monoethanolamine Feed Rate kg/m³ | Ammonia to Monoethanolamine mole Ratio | Hydrogen, Mole % of Ammonia | Temperature °C. | Pressure atm. absolute | Monoethanolamine Conversion Rate, % | Reaction Product Distribution, (wt. %) | | | | |
|---|---|---|---|---|---|---|---|---|---|---|---|
| | | | | | | | Diethylenetriamine | Piperazine | Aminoethylethanolamine | Ethylenediamine | Substituted Piperazine |
| 1 | 940 | 18.1 | 13.2 | 175 | 150 | 36 | 13.14 | 5.36 | 11.14 | 70.1 | 0.30 |
| 2 | 810 | 14.7 | 9.3 | 176 | 150 | 38.5 | 19.11 | 8.37 | 8.93 | 62.09 | 1.50 |
| 3 | 890 | 21.5 | 9.3 | 176 | 150 | 35.1 | 17.07 | 5.96 | 6.77 | 69.31 | 0.89 |
| 4 | 460 | 19.6 | 7.5 | 176 | 150 | 49.9 | 12.19 | 9.17 | 8.03 | 69.32 | 1.28 |
| 5 | 490 | 19.8 | 7.9 | 175 | 150 | 47.4 | 11.75 | 7.32 | 8.29 | 70.98 | 1.66 |
| 6 | 610 | 20.6 | 6.7 | 175 | 150 | 44.3 | 9.69 | 6.66 | 8.71 | 74.48 | 0.46 |
| 7 | 460 | 19.2 | 8.3 | 174 | 150 | 52.5 | −11.32 | 9.50 | 9.69 | 69.38 | 0.11 |
| 8 | 610 | 17.9 | 8.8 | 175 | 150 | 45.8 | 9.24 | 7.21 | 9.45 | 74.00 | 0.09 |
| C-1 | 610 | 14.0 | 9.4 | 194 | 175 | 45.2 | −11.1 | 10.7 | 5.2 | 70.4 | 2.6 |
| C-2 | 260 | 14.0 | 8.0 | 175 | 125 | 73.4 | 12.9 | 17.1 | 8.9 | 57.1 | 4.0 |
| C-3 | 890 | 19.1 | 4.1 | 175 | 150 | 34.6 | 9.35 | 4.90 | 8.11 | 77.65 | — |
| C-4 | 860 | 19.2 | 7.6 | 184 | 150 | 61.3 | 6.81 | 23.11 | 4.12 | 49.72 | 16.25 |
| C-5 | 840 | 20.2 | 7.3 | 175 | 150 | 27.7 | 7.01 | 3.86 | 10.96 | 77.97 | 0.2 |
| C-6 | 920 | 20.1 | 9.4 | 175 | 150 | 29.8 | 7.21 | 4.40 | 10.06 | 78.33 | — |

What is claimed is:

1. A process for producing diethylenetriamine from ethanolamine containing at least about 70 mole percent monoethanolamine comprising continuously passing an amination feedstream comprising the ethanolamine, ammonia and hydrogen over a reductive amination catalyst in a reaction zone under reductive amination conditions at a rate sufficient to provide at least about 400 kilograms of ethanolamine per hour per cubic meter of reaction zone containing catalyst sufficient to produce less than about 10 weight percent piperazine based on the reaction products and at a temperature sufficient to react between about 35 and 60 percent of the ethanolamine fed, said rate and temperature being sufficient to result in the quantity of the weight percent of aminoethylethanolamine produced based on total reaction products times the percent conversion of ethanolamine being less than about 600.

2. The process of claim 1 wherein the reductive amination conditions comprise a pressure between about 35 and 400 atmospheres absolute and a temperature between about 150° and 225° C.

3. The process of claim 1 wherein the rate and temperature are sufficient to react between about 45 and 55 percent of the ethanolamine.

4. The process of claim 3 wherein the reductive amination conditions comprise a pressure between about 40 amination catalyst comprising at least one of nickel, cobalt, iron and copper in a reaction zone at a pressure of about 40 to 200 atmospheres absolute and a temperature of about 170° to 225° C., at a rate sufficient to provide 450 to 1000 kilograms of ethanolamine per hour per cubic meter of reaction zone containing catalyst, said temperature and rate being sufficient to react between about 38 and 58 percent of the ethanolamine and produce less than about 10 weight percent piperazine based on total reaction products.

11. The process of claim 10 wherein said rate and temperature are sufficient to result in the quantity of the weight percent of aminoethylethanolamine produced based on total rection products times the percent conversion of ethanolamine being less than 600.

12. The process of claim 10 wherein the mole ratio of ammonia to ethanolamine in the amination feed is between about 4:1 to 25:1 and the hydrogen is provided in an amount of about 4 to 12 mole percent based on ammonia.

13. The process of claim 10 wherein the feedstream comprises ethylenediamine in a mole ratio to ethanolamine of about 0.1:1 to 1:1.

14. The process of claim 10 wherein the gas hourly space velocity of the amination feedstream is in the range of about 12 to 60 reciprocal hours.

* * * * *